(12) United States Patent
Howe

(10) Patent No.: US 11,872,331 B2
(45) Date of Patent: Jan. 16, 2024

(54) PATHOGEN INACTIVATION DEVICE

(71) Applicant: SouthPac Trust International Inc., Rorotonga (CK)

(72) Inventor: Leslie David Howe, Ottawa (CA)

(73) Assignee: SOUTHPAC TRUST INTERNATIONAL, INC.

( * ) Notice: Subject to any disclaimer, the term of this patent is extended or adjusted under 35 U.S.C. 154(b) by 0 days.

(21) Appl. No.: 17/346,613

(22) Filed: Jun. 14, 2021

(65) Prior Publication Data
US 2022/0395604 A1 Dec. 15, 2022

(51) Int. Cl.
*A61L 9/20* (2006.01)

(52) U.S. Cl.
CPC ............ *A61L 9/20* (2013.01); *A61L 2209/12* (2013.01)

(58) Field of Classification Search
None
See application file for complete search history.

(56) References Cited

U.S. PATENT DOCUMENTS

| | | | | |
|---|---|---|---|---|
| 4,091,441 A | * | 5/1978 | Ott | A61N 5/0618 315/153 |
| 6,739,734 B1 | * | 5/2004 | Hulgan | F21S 8/026 362/217.05 |
| 2009/0004046 A1 | * | 1/2009 | McEllen | H05B 41/39 422/2 |
| 2016/0010820 A1 | * | 1/2016 | Vasylyev | B29D 11/00663 359/595 |
| 2021/0220506 A1 | * | 7/2021 | Kirschman | A61L 2/26 |
| 2022/0008602 A1 | * | 1/2022 | Sood | A61L 2/10 |
| 2022/0111105 A1 | * | 4/2022 | Pan | A61L 9/20 |
| 2022/0218864 A1 | * | 7/2022 | Tribble | A61L 9/20 |

FOREIGN PATENT DOCUMENTS

| | | | | | |
|---|---|---|---|---|---|
| CN | 111365651 A | * | 7/2020 | | |
| RU | 2121629 C1 | * | 11/1998 | | A61L 9/20 |
| WO | WO-9517634 A1 | * | 6/1995 | | A61L 9/20 |

* cited by examiner

*Primary Examiner* — Andrew Smyth
(74) *Attorney, Agent, or Firm* — McDonald Hopkins LLC

(57) ABSTRACT

An example embodiment of an upper room air germicidal light fixture may comprise a light source configured to emit germicidal light and may further comprise one or more lower and upper baffle assemblies disposed adjacent to the light source. Said upper and lower baffle assemblies may be configured to enable air to flow through them and to block or substantially dissipate incident light rays from the light source. One or more apertures may be defined by the openings between a corresponding set of upper and lower baffle assemblies, wherein said light can exit the fixture through said apertures. When the germicidal light fixture is disposed in a room, surrounding room air may contact light exiting the apertures of said fixture, and room air traveling through said fixture may contact light inside and between the one or more upper and lower baffle assemblies.

14 Claims, 17 Drawing Sheets

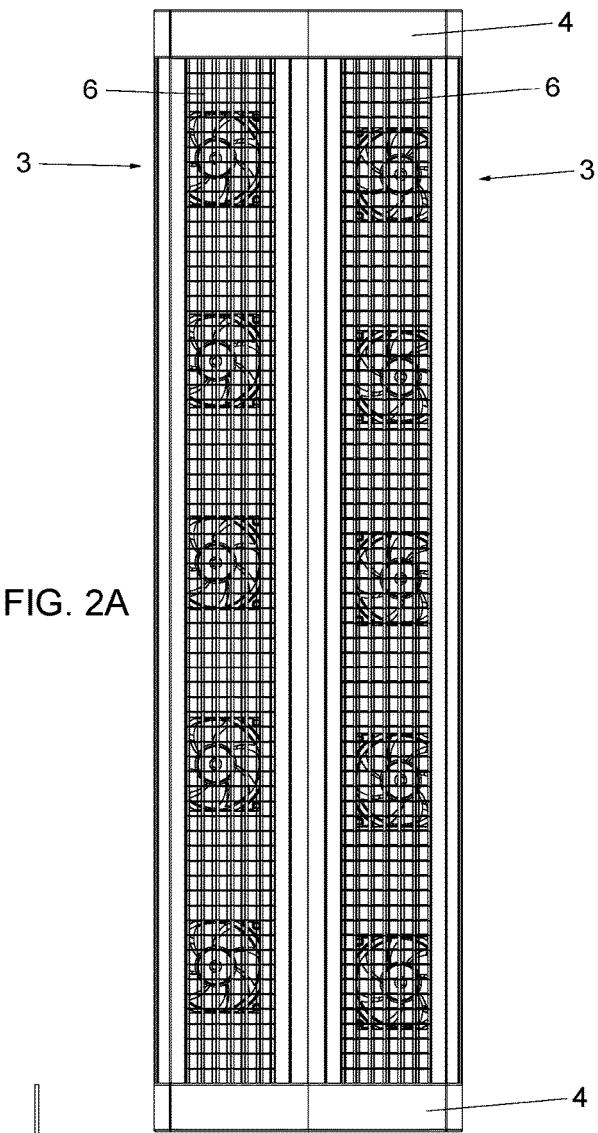
FIG. 2A
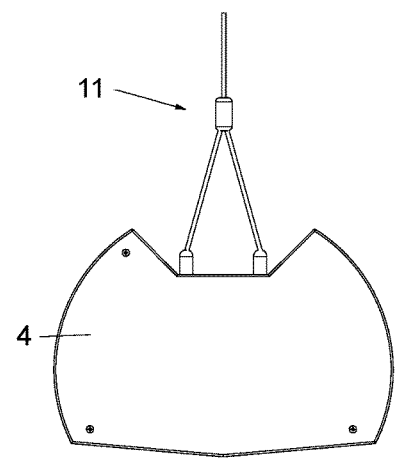
FIG. 2B
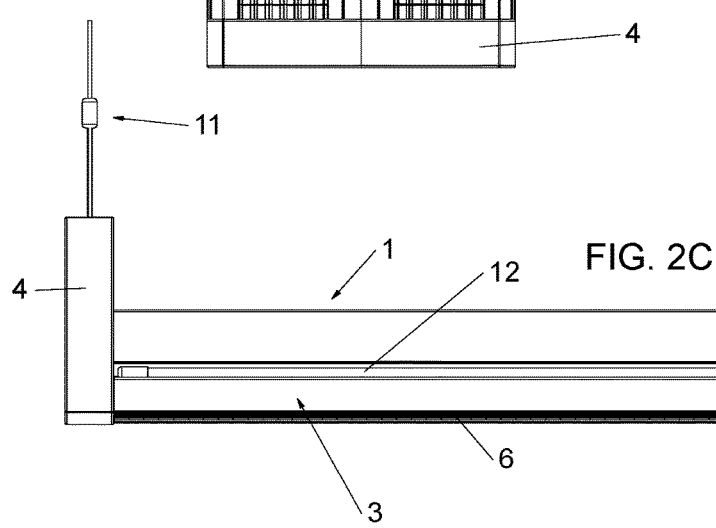
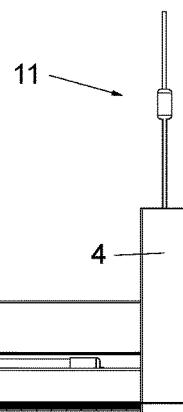
FIG. 2C

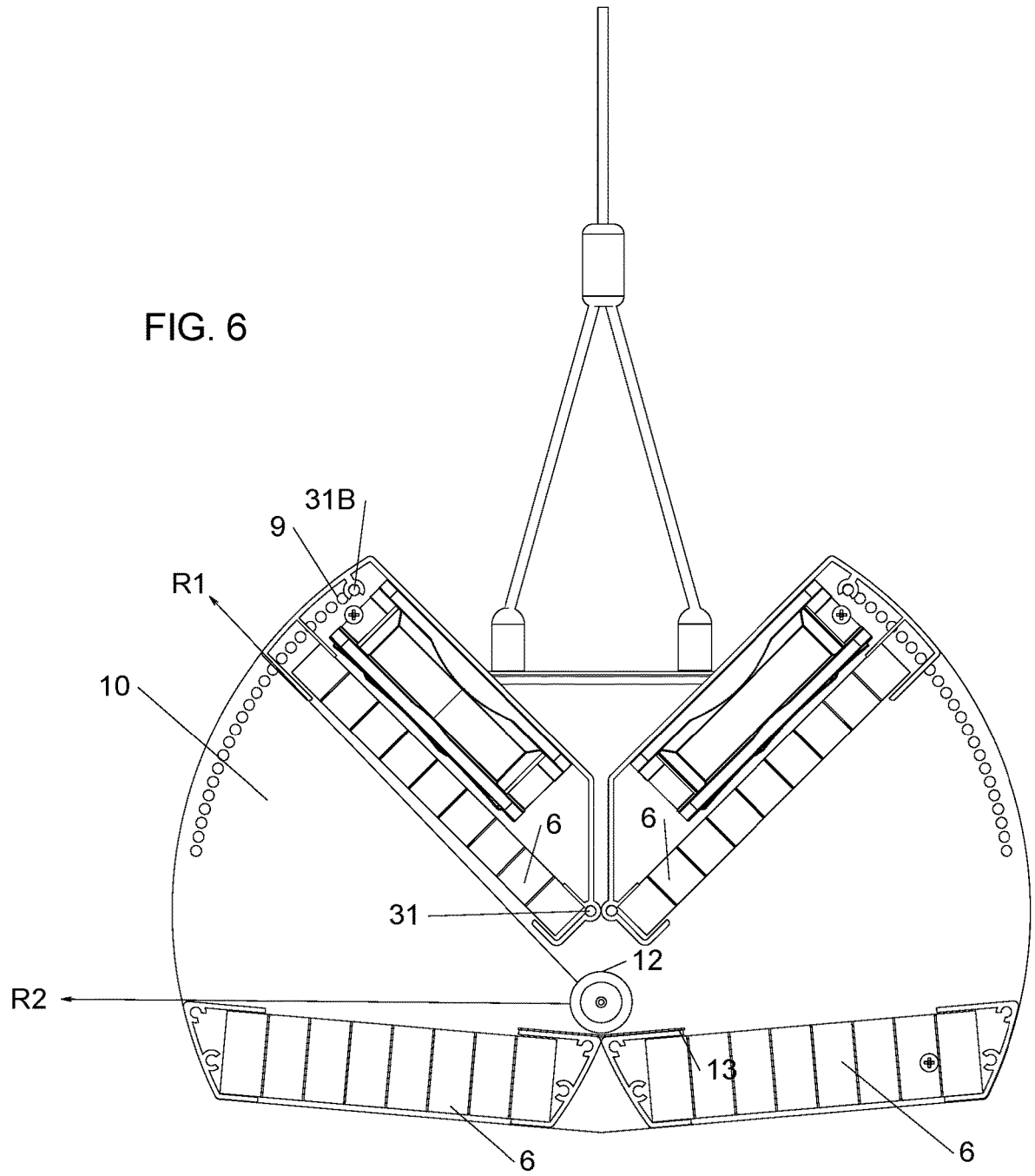

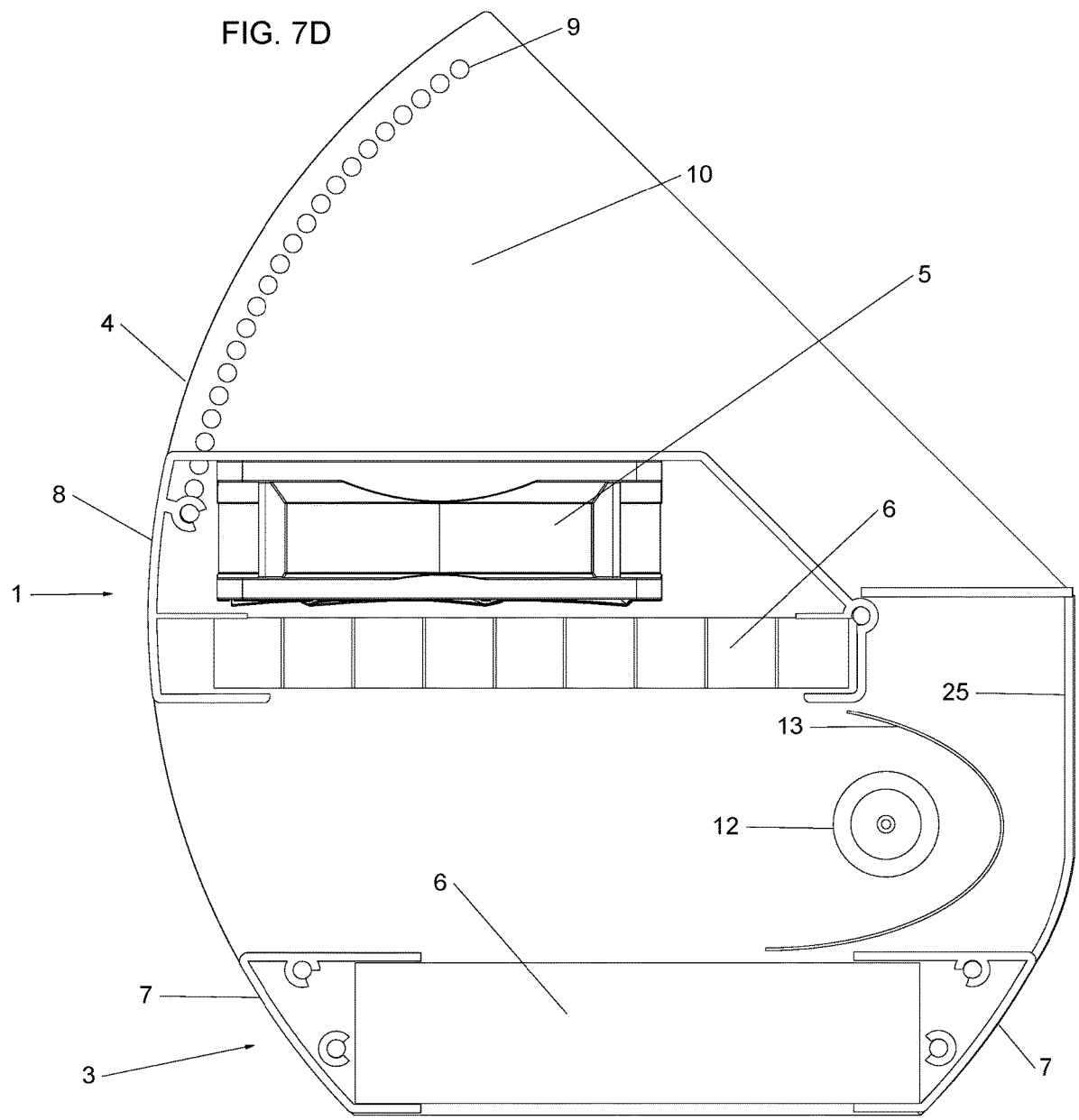

FIG. 9A
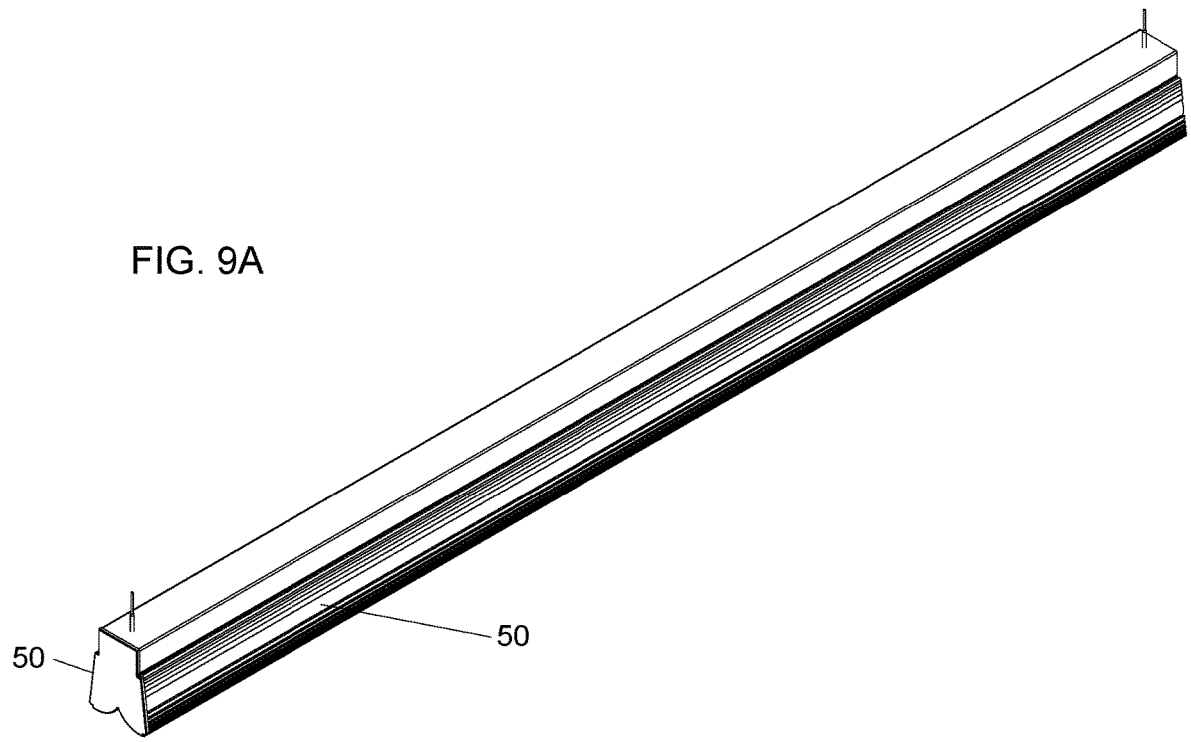
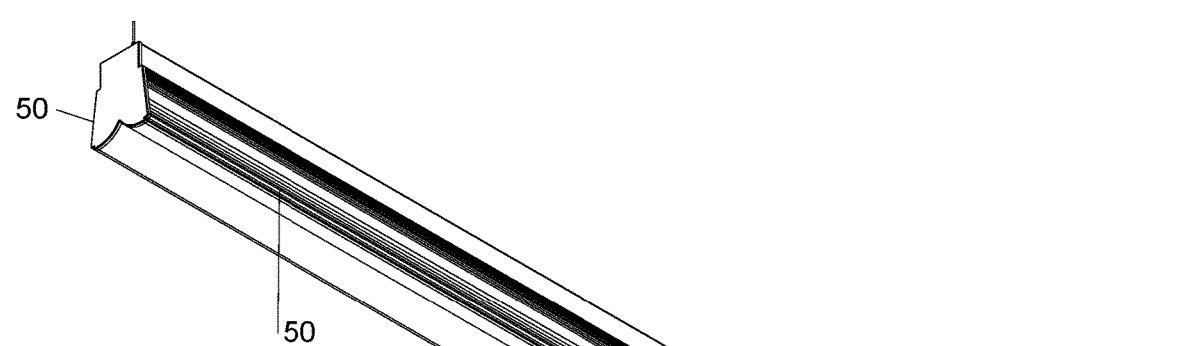
FIG. 9B

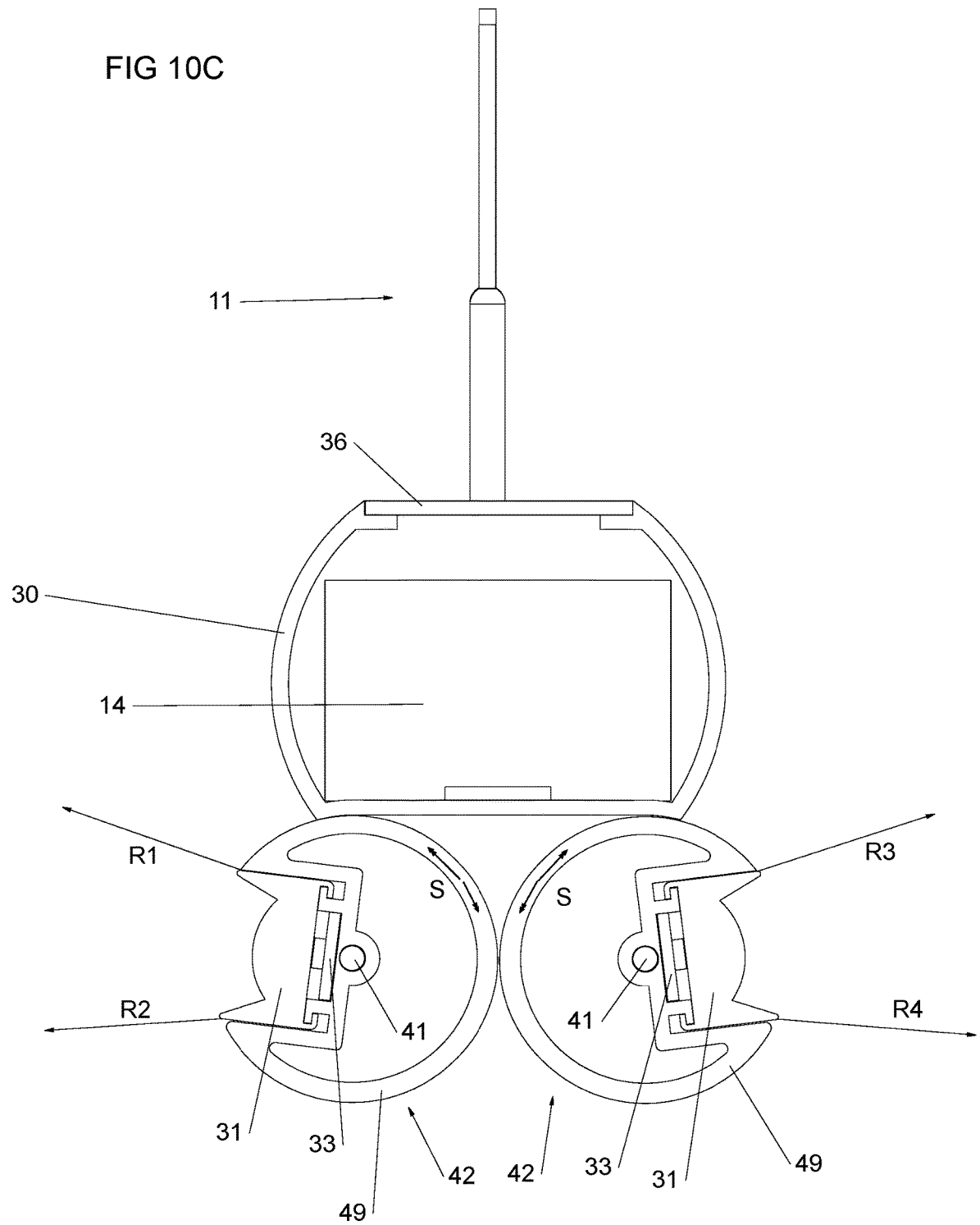

PATHOGEN INACTIVATION DEVICE

CROSS REFERENCE TO RELATED APPLICATIONS

This application claims the benefit of the following United States Provisional Patent Application, the contents of which are incorporated by reference in their entirety as if set forth in full: U.S. Provisional Patent No. 63/039,668 entitled "PATHOGEN INACTIVATION DEVICE" filed Jun. 16, 2020.

TECHNICAL FIELD

This disclosure generally relates to germicidal fixtures that are capable of inactivating pathogens.

BACKGROUND

There is a continuing need for devices that can kill or reduce airborne pathogens.

BRIEF DESCRIPTION OF THE FIGURES

FIG. 2A shows a bottom plan view of the example embodiment of germicidal light fixture shown in FIG. 1B FIG. 2B shows an end profile view of the example embodiment of germicidal light fixture shown in FIG. 1B.

FIG. 2C shows a side profile view of the example embodiment of germicidal light fixture shown in FIG. 1B.

FIG. 6 shows an end view of the example embodiment of germicidal light fixture shown in FIG. 1B with certain elements removed for illustrative purposes and includes light ray propagation diagrams.

FIG. 7D shows an end view of the example embodiment of germicidal light fixture shown in FIG. 7A with certain elements removed for illustrative purposes.

FIG. 9A shows a top perspective view of an example embodiment of the germicidal light fixture comprising one or more lenses.

FIG. 9B shows a bottom perspective view of the example embodiment of germicidal light fixture shown in FIG. 9A.

FIG. 10C shows an end view of the example embodiment of the germicidal light fixture shown in FIG. 10A with certain elements removed for illustrative purposes.

DETAILED DESCRIPTION

Figure 11:
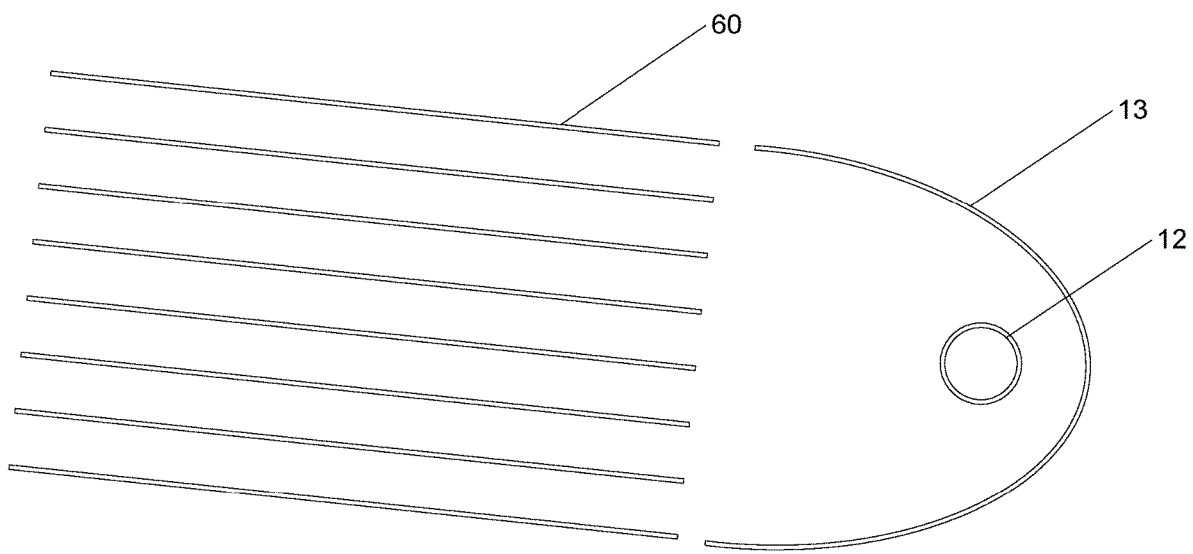
FIG. 11 shows a simplified cross-sectional view of a lens and reflector system of a typical upper room GUV fixture.

Upper room air germicidal fixtures may have been manufactured and used for many decades. They may typically comprise a 254 nm UVC lamp with a set of multiple deep parallel black louvers in front of the lamp. The fixture may or may not contain a parabolic reflector disposed around the lamp to collimate the light rays from the lamp as best as possible, wherein said light rays may pass through the louvers with as few reflections as possible. FIG. 11 shows a simplified example with louvers 60, light source 12, and reflector 13. On fixtures with single lamps, a reflector around the lamp may necessitate that a fixture is limited to emitting UVC light on one side of the fixture only. The current state of the art of upper room air GUV ("germicidal UV") fixtures may have several inherent disadvantages. These disadvantages may include extremely high optical losses, lack of beam angle adjustability to account for spaces with different ceiling heights, and the requirement of room fans to increase air mixing to increase fixture efficacy. Air mixing may have a high correlation to the efficacy and kill ratios of a given GUV fixture. Other disadvantages may include very heavy weight and visually unappealing industrial looking designs. If some or all of these disadvantages could be improved upon, a truly novel upper room air GUV fixture may be realized. Example embodiments disclosed in this application may eliminate or improve upon some or all of these disadvantages.

Although various embodiments of the invention may be described with respect to upper room air GUV fixtures, this is for illustrative purposes only, and should not be construed to limit the scope of possible applications for the various embodiments of the invention. The written descriptions may use examples to disclose certain implementations of the disclosed technology, including the best mode, and may also to enable any person skilled in the art to practice certain implementations of the disclosed technology, including making and using any devices or systems and performing any incorporated methods. The patentable scope of certain implementations of the disclosed technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The light source may be described in various example embodiments as being UVC light. It should be noted that the term "UVC" is being used as an example spectrum of germicidal light and should not serve to limit the intended wide scope of germicidal light spectrums or wavelengths as is intended. For example, example embodiments of GUV fixture may utilize UVA or UVB spectrums and may also utilize specific wavelengths of light such as 222 nm, or subsets of wavelengths of a given light spectrum.

Materials used to fabricate various elements of example embodiments that are not of a novel nature, or that would be obvious to a person skilled in the art may or may not be discussed herein. For example, many structural parts may be fabricated from materials that are suitably non reflective to the spectrum of light utilized by the fixture's light source and materials that will not appreciably degrade over time etc. such as aluminum sheet metal or extrusions painted, powder coated or anodized with flat black paint. Omission of notation or discussion of any said materials should not be construed to limit the scope of any example embodiments of GUV fixtures herein.

Figure 1A:
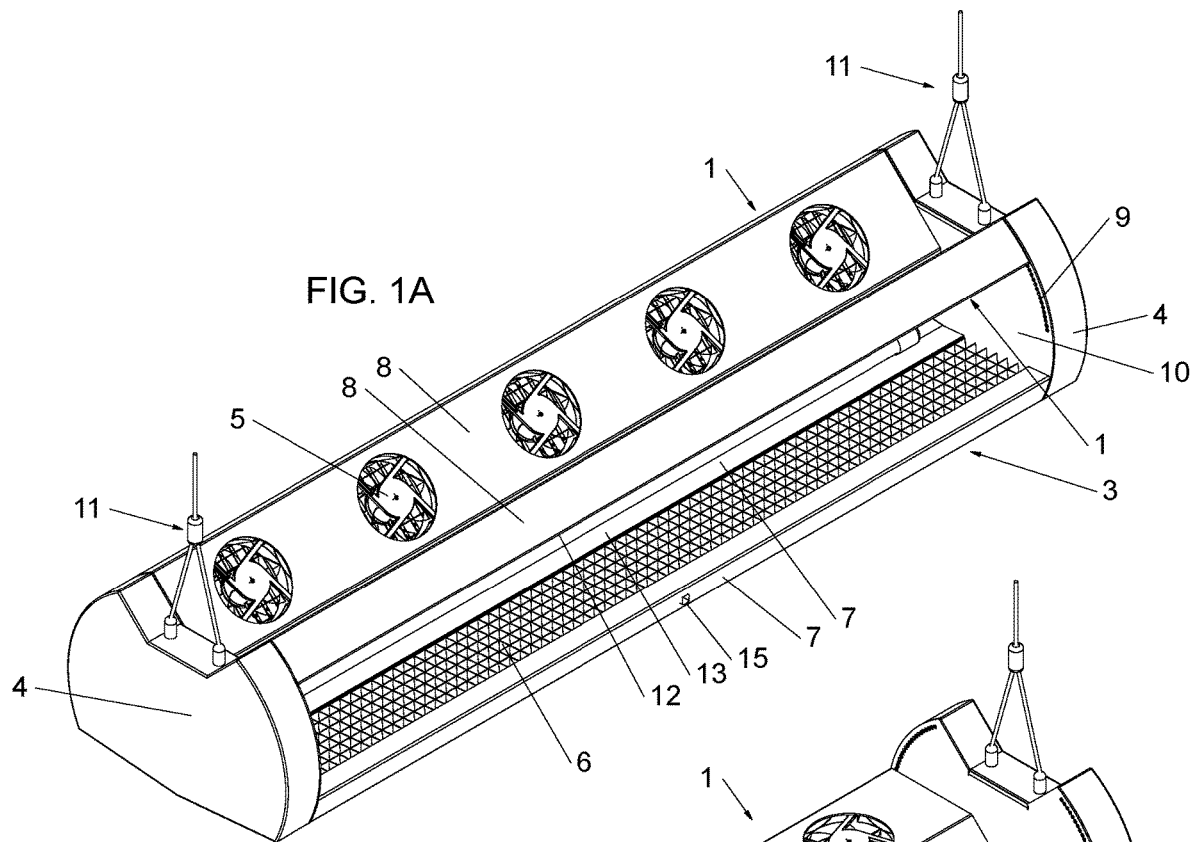
FIG. 1A shows a top perspective view of an example embodiment of germicidal light fixture configured with its upper baffle assemblies adjusted for high ceiling rooms.
Figure 1B:
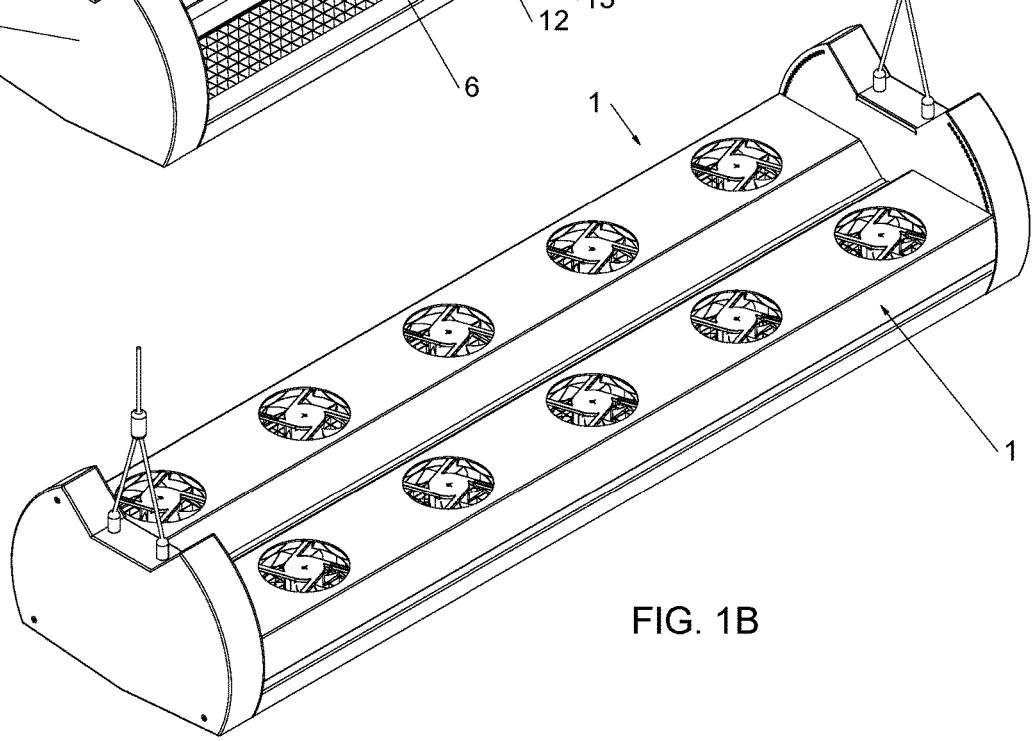
FIG. 1B shows a top perspective view of the example embodiment of germicidal light fixture shown in FIG. 1A except configured with its upper baffle assemblies adjusted for low ceiling rooms.

An example embodiment of a GUV fixture is shown in FIGS. 1A and 1B in two different perspective views. FIG. 1A shows an example embodiment configured with the upper baffle assemblies 1 at an approximate angle of 45 degrees from horizontal. This configuration may be appropriate in spaces with tall ceilings, commonly referred to as "high bay" applications. A light source 12 may comprise any light source comprising germicidal properties capable of inactivating one or more types of pathogens. Examples may include but are not limited to 254 nm mercury discharge lamps, 222 nm krypton-chlorine excimer lamps, and LED tubes or arrays. Although example embodiments discussed may be shown comprising a T5 style germicidal lamp for illustrative purposes, this should not be construed to limit the scope of possible different light sources.

A reflector 13 may be configured from any suitably efficient reflective material for the given wavelength of the light source 12. For example, aluminum tape or polished aluminum sheet metal which may function to decrease light absorption losses from the light source 12.

Referring to an example embodiment of GUV fixture as shown in FIG. 1B configured with the upper baffle assemblies 1 adjusted to an approximate angle of 10 degrees from horizontal. This configuration shown may be appropriate for low ceiling applications, perhaps in the 9 ft. range. Referring to a cross sectional view of an example embodiment shown in FIG. 4, an example light ray R2 from the light source 12 may represent the lower edge of the beam angle of light radiated from the fixture. Note that this lower edge may be approximately parallel to the floor in a room the fixture may be mounted in. This may avoid any UVC light from striking occupants that may be disposed below the fixture. R1 may represent the upper edge of the beam angle. Selectively limiting the upper edge of the beam angle may avoid ceiling reflections that may reflect down on room occupants. It should be noted that even extremely small irradiance levels, when considered in relation to an 8-hr. day, may create a potentially unsafe dosage level to room occupants.

With the aperture configuration as shown in FIG. 1B configured for low ceilings, the fixture efficiency may be near its lowest level. If the fixture utilizes a UV lamp with an output of 23 watts, and both opposing apertures are adjusted to an opening of 12 degrees, the total UV light exiting the apertures may have a radiant flux of approximately 2.2 watts. The fixture efficiency may be around 9.5% which may still be significantly higher than the 1-2% efficiency range of current upper room GUV fixtures utilizing traditional optics as previous discussed.

Referring to FIG. 6 in an example embodiment, the end plates 10 may comprise an array of upper baffle assembly positioning holes 9. Said holes 9 may be configured on a radius that may be concentric with pivot holes 31. Holes 31B in the upper baffle assemblies 1 may align with holes 9 in end plates 10 and may be attached with any fastening means that may suit an application, such as screws, pins or quick release fasteners for example. The upper baffle assembly positioning holes 9 may be spaced at any suitable interval, such as every two degrees for example. Accordingly, the upper baffle assemblies may be adjustably configurable to allow for an adjustable aperture wherein more or less UVC light may be output from an example embodiment of GUV fixture. Increasingly larger beam angles beginning from the initial lowest setting as discussed in reference to FIG. 4 may be utilized for correspondingly increased room ceiling heights. As each aperture is increased, more direct light from the light source may be allowed to exit the fixture. Increased ceiling heights may in turn increase the travel distance for UVC light rays to strike a ceiling surface, and subsequently reflect downwards to an occupied zone of the room. Considering the inverse square law, the angle of the upper baffle assemblies may be configured on-site such that irradiance levels from an example embodiment of GUV fixture may be of an acceptably safe level for room occupants.

Referring to FIG. 6 in an example embodiment, UVC light rays R1 and R2 may represent an approximate 45-degree beam angle of light distribution emitted from the light source 12, from each side of the fixture. Assuming the light source 12 is a 254 nm T5 HO lamp with a total radiant flux of 23 watts, the approximate fixture output may be about 7 watts with a fixture efficiency of about 30%. Many current GUV fixtures on the market may exhibit efficiencies in the range of 1-2 percent with a fixture aperture.

Figure 3:
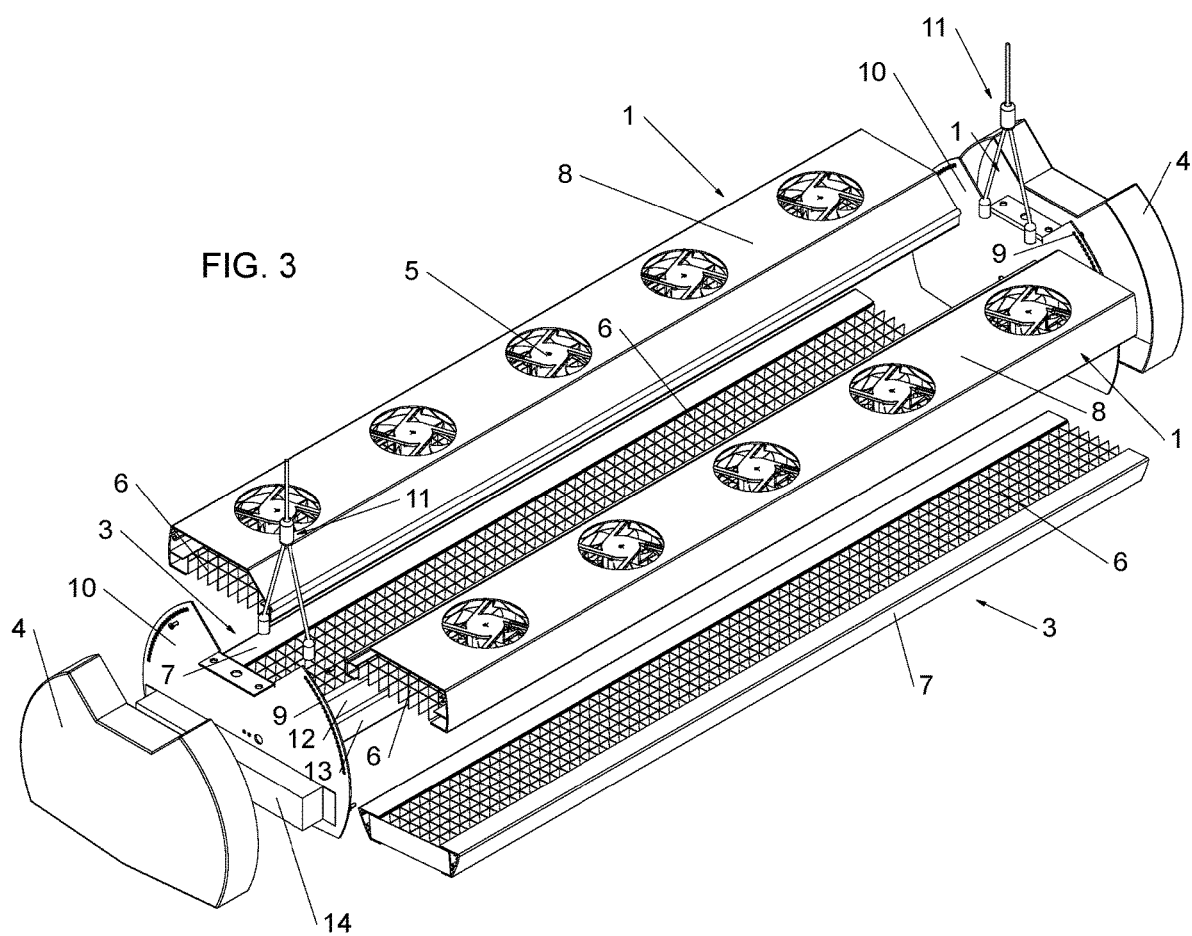
FIG. 3 shows an exploded view of the example embodiment of germicidal light fixture shown in FIG. 1B.

Referring to FIG. 1A in an example embodiment, opposing upper baffle assemblies 1 and opposing lower baffle assemblies 3 are shown. Referring to FIG. 3 in an exploded view, the lower baffle assemblies 3 may comprise support rails 7 and egg crate louvers 6. The upper baffle assemblies may comprise support rails 8, egg crate louvers 6 and fans 5. The egg crate louvers 6 may be fabricated from any appropriate material that may serve to block UVC light and reflect as little light (both diffuse and specular) as possible and wherein the material does not significantly degrade over time due to the UVC light. Flat black aluminum may be a cost effective choice. PPFE plastic may also be effective. It can be shown from studies that 254 nm light may reflect differently than light in the visible spectrum. For example, some high efficiency mirrors may act as opaque absorbers to 254 nm light. Therefore, care must be taken to choose and appropriate material for the egg crate louvers.

Figure 4:
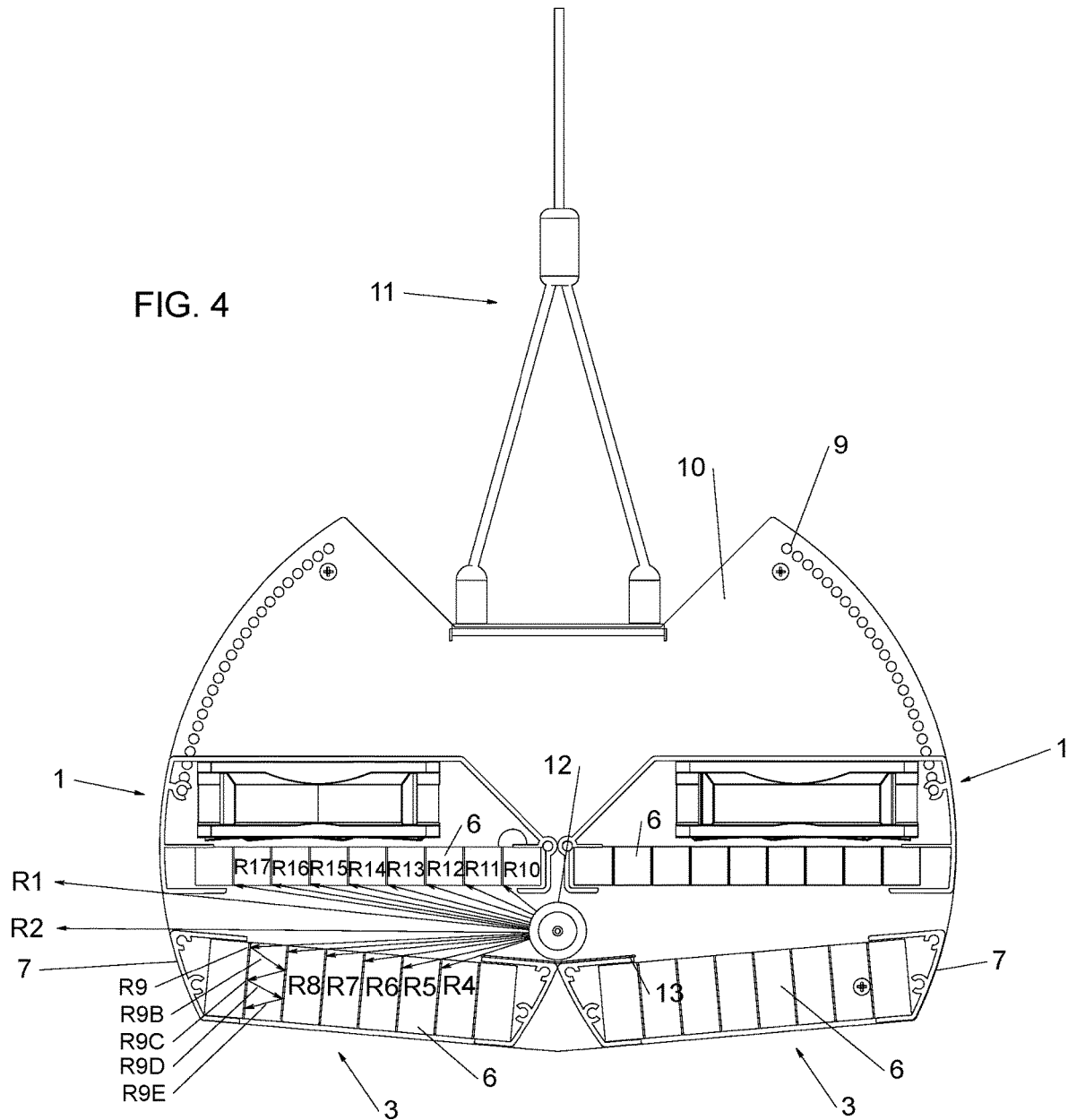
FIG. 4 shows an end view of the example embodiment of germicidal light fixture shown in FIG. 1B with certain elements removed for illustrative purposes and includes light ray propagation diagrams.

FIG. 4 shows an example embodiment of GUV fixture configured for low ceilings as shown with example light rays R1 and R2 emanating from the light source 12, indicating the upper and lower limits of the beam angle of light dispersed from the example embodiment of GUV fixture. Example light rays R4 through R9 may be on a trajectory that may be too shallow to exit the aperture between R1 and R2 and may therefore strike the egg crate 6. For illustrative purposes, assuming that the reflections of the light rays R4 through R9 off the egg crate 6 surfaces are specular, the law of reflections and the acute angles of incidence may cause one or more reflections inside each corresponding egg crate louver cell, which may diminish the intensity of any specular reflections to a negligible flux level wherein any light rays that exit the bottom of the egg crate cells will have little to no effect on occupants below. For example, light ray R9 and subsequent example specular reflections R9B through R9E are shown. Assuming a reflection efficiency of black painted aluminum of approximately 5%, each of the subsequent reflections R9B through R9E my exhibit an approximate 95% reduction in intensity. Accordingly, any UVC light that may exit the egg crate louvers 6 may be of negligible flux intensity. Upper baffle assemblies 1, lower baffle assemblies 3, end plate 10, upper baffle assembly positioning holes 9, hanger assembly 11, and lower baffle assembly mounting rails 7 are also notated in FIG. 4.

A similar analogy may be applied to diffuse reflections from R4 through R8 in the cells of the lower egg crate louver 6. Also, a similar analogy may be applied to example light rays R10 through R17 striking the cells of the egg crate louvers 6 shown in the upper baffle assemblies 1.

As discussed, the egg crate louvers 6 disposed adjacent to the lamp 12 may serve a similar function as the long parallel louvers 60 shown in FIG. 11. In FIG. 11, a parabolic reflector 13 surrounds the light source 12. FIG. 11 may represent a traditional upper room GUV fixture system, wherein the reflector 13 may serve to partially columnize the light rays exiting the light source 12 before entering the louvers 60. The louvers 60 may function to further columnize the light rays such that the beam angle of the light exiting the louvers is in a tight dispersion pattern (approximate 5-6 degrees perhaps). Due to the upward orientation of the louvers 60 at an angle of approximately 5-6 degrees, the lower edge of the UVC light beam exiting the fixture may travel approximately horizontal in a given room. In example embodiments if the instantly disclosed invention, the egg crate louvers 6 disposed adjacent to a light source 12 (FIG. 4) may function in a similar manner, but also may represent a novel improvement thereof.

Figure 5:
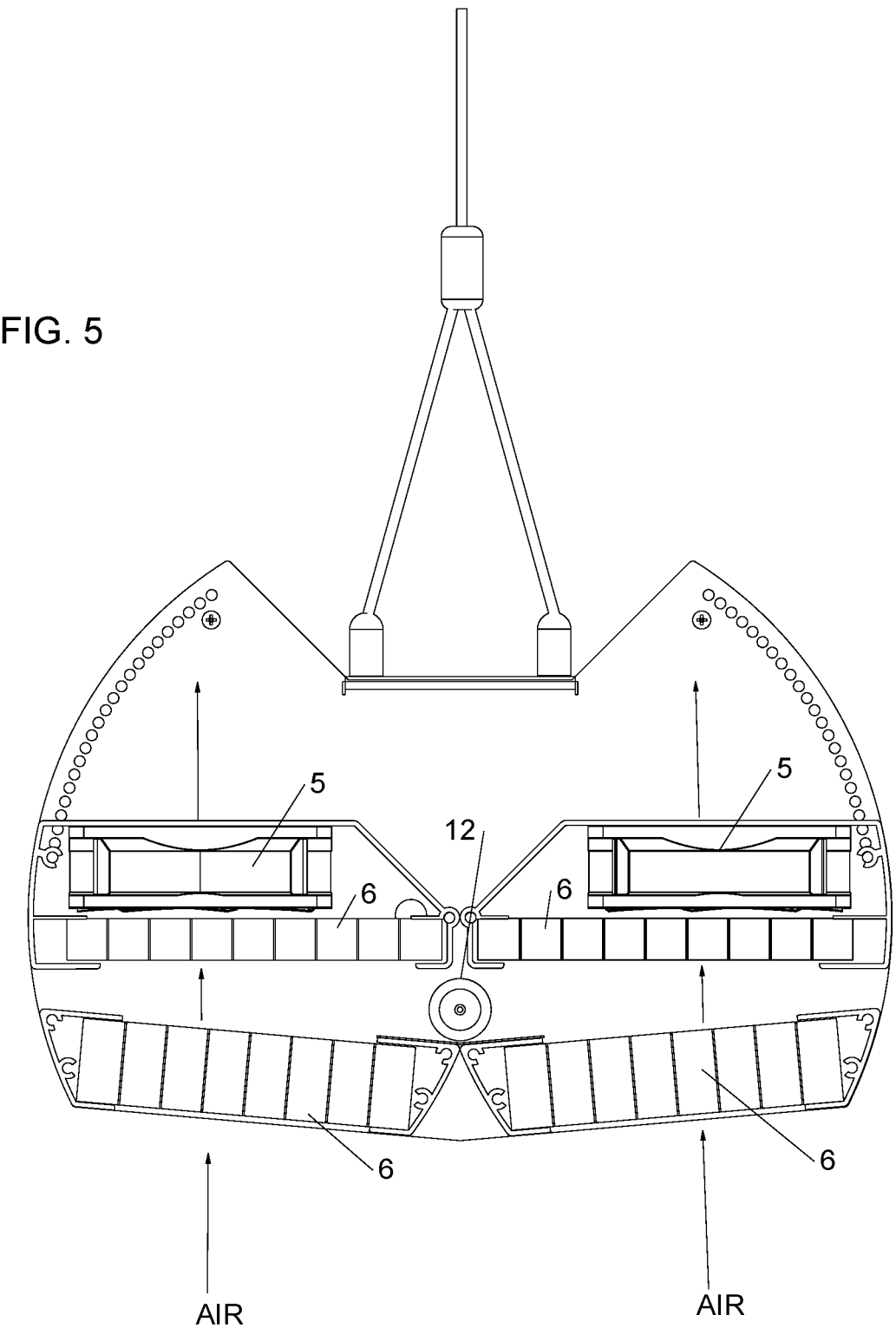
FIG. 5 shows an end view of the example embodiment of germicidal light fixture shown in FIG. 1B with certain elements removed for illustrative purposes and includes air flow diagrams.

As shown in FIG. 4, the egg crate louvers disposed adjacent to the light source as shown may function to block or significantly dissipate light rays from exiting the fixture that are not able to exit directly through the apertures between light rays R1 and R2, and thus may function as an efficient and effective baffle. Any light striking the egg crate louvers 6 may dissipate within the egg crate louver cells, thereby minimizing any UV light reflecting above or below the beam angle created by the apertures. As shown in FIG. 5 in an example embodiment, a novel feature of the disclosed invention may be that the egg crate louvers 6 in the lower baffle assemblies 3 may allow air to flow relatively freely upwards through them both due to the stack effect in the room the fixture may be disposed in, as well as the partial vacuum created underneath the fans 5 in the upper baffle assemblies 1. Air flow may then exit the top of the fans 5. The arrows denoted as "Air" may show a simplified airflow diagram through the fixture.

Although example embodiments of GUV have been described as having upper and lower baffle assemblies comprising egg crate louvers, alternate baffle designs may also be utilized. Since the baffle may function to predominately block or dissipate certain light rays outside the desired fixture beam angle and also to allow air to flow through the baffles, any alternate baffle design that can function similarly may also be utilized. For example, instead of utilizing an egg crate louver, a strip of material oriented in a similar orientation as the egg crate louver in example embodiments may be utilized. The fabric may need to allow air to pass through it as well as having a high absorption rate for the frequency of light emitted by the light source may. For example, fabric style air filter material such as activated carbon for example that may absorb UVC may be utilized.

As previously discussed, UVC light from the light source 12 may exit the fixture through the aperture formed between the upper and lower baffle assemblies (example light rays R1 and R2 in FIG. 4) or dissipate within the egg crate cells. However, the prime function of an upper room air GUV fixture may be to irradiate as large a volume of air as possible in a room every hour. Conventional upper room GUV (as shown in FIG. 11) fixtures may only irradiate the room air with UVC once the light exits the fixture. Consequently, the efficacy of the fixture may be severely limited as previously discussed. In example embodiments of the disclosed invention as discussed, the air passing through the fixture due to the fans (Feature 5 in FIG. 5 for example) and the room stack effect may be irradiated inside the cells of the egg crate louvers, and to a greater extent, the space between the upper and lower baffle assemblies.

This novel action may function to significantly increase the efficacy of example embodiments of the disclosed technology. Pathogen inactivation may be determined by irradiance multiplied by time. Typical irradiance values of UVC from an upper room GUV fixture may be as high as 250 uw/cm2 at one meter distance from the light source and may decay according to the inverse square law. However, in example embodiments of GUV fixtures, the irradiance levels inside the fixture may range from 2500 to 10,000+ uw/cm2. Since air may be traveling through the fixture through extremely high irradiance levels in addition to the radiant flux distributed into a given space through the apertures, the overall efficacy of example embodiments of GUV fixture may be exponentially greater.

Additionally, as previously described, the novel adjustable aperture features of example embodiments may allow efficiencies of 9.5% to 30% of UVC when comparing the output from the light source (with a UVC lamp having and output of 23 watts for example) vs the UVC light exiting the fixture. Thus, the increased efficacy of example embodiments of GUV fixtures may be truly novel and represent a significant advancement in upper room GUV technology.

Example embodiments of GUV incorporating fans may also be advantageous in that addition room air mixing devices such as paddle fans may not need to be utilized. This may save on the costs of the paddle fans, installation and may eliminate any possible negative aesthetic aspects of said paddle fans.

Inherently, UVC dispersion above the heads of the occupants may present a danger of accidental over-exposure for anyone entering the UVC irradiated zone, such as trade's people on ladders for example. In an example embodiment as shown in FIG. 1A, the GUV fixture may comprise a motion sensor 15, wherein any person entering a preset zone surrounding the light fixture may subsequently switch off the example embodiment of GUV fixture for a preset length of time. In example embodiments, there may one or more sensors 15 attached, and the one or more sensors may be located at any best utilized position(s) on the fixture for a given application.

Referring to FIG. 4 in an example embodiment, a reflector 13 as previously discussed may be placed underneath the light source 12. The reflector 13 may function to redistribute UVC light that may be incident on its surface and redistribute and recycle it inside the fixture. This recycled UVC light may subsequently contact air within or outside the fixture which may increase the overall efficacy of the fixture.

Referring FIG. 3, a ballast (or LED driver if the light source comprises LED arrays) 14 to power the light source 12 may be attached to an end plate 10 or may be attached to the inside of an end cap 4. These mounting arrangements may also apply to a power supply for the fans 5 (not shown) and associated wiring for the fixture's associated parts. An advantage of mounting said items in the end cap 4 may be that replacement of the ballast 4, wiring and fan power supply (not shown) may be more easily implemented in the field.

In an example embodiment as shown in FIG. 1A, the fans 5 may comprise computer CPU fans. CPU fans may have the advantage of being perhaps the most ubiquitous, most scientifically engineered cost competitive small fans available. For example, in an example embodiment of GUV fixture, 10 installed and tested very low-cost fans may be able to move 24,000 cubic feet of air per hour through an example embodiment of GUV fixture, and may be relatively inaudible over normal room ambient noise.

Referring to FIG. 1A, example embodiments of GUV fixtures may be hung from ceiling with pendant style hanger assemblies 11. Other fixture mounting methods may utilized as well, such as wall mounting which may be discussed at a later point in this disclosure.

An example embodiment of GUV fixture as shown in FIG. 1A may comprise upper baffle assemblies 1, lower baffle assemblies 3, end caps 4, fans 5, egg crate louvers 6, lower baffle assembly rails 7, upper baffle assembly rails 8, upper baffle assembly positioning holes 9, end plates 10, hanger assemblies 11, lamp 12, optional reflector 13 and motion sensor 15.

An example embodiment of GUV fixture as shown in FIG. 1B may comprise upper baffle assemblies 1.

A view of the bottom side (floor facing after installed in a hanging position in a room) in an example embodiment of GUV fixture is shown in FIG. 2A, and may comprise lower baffle assemblies 3, egg crate louvers 6 and end caps 4.

An end profile view of an example embodiment of GUV fixture is shown in FIG. 2B and may comprise end caps 4 and hanger assemblies 11.

A side view of an example embodiment of GUV fixture is shown in FIG. 2C, and may comprise lower baffle assemblies 3, upper baffle assemblies 1, egg crate louvers 6, lamp 12, hanger assemblies 11 and end caps 4.

An exploded view of an example embodiment of GUV fixture is shown in FIG. 3 and may comprise upper baffle assemblies 1, lower baffle assemblies 3, end caps 4, fans 5, egg crate louvers 6, lower baffle assembly rails 7, upper baffle assembly rails 8, upper baffle assembly positioning holes 9, end plates 10, hanger assemblies 11, lamp 12, optional reflector 13, and ballast 14.

Example embodiments of the disclosed technology may also include GUV fixtures configured to mount on walls. FIG. 7C shows an example embodiment of GUV fixture with a single upper baffle assembly 1 and a single lower baffle assembly 3 and may be attached to a wall 26 wherein a fixture mounting plate 25 may attach the wall 26.

Figure 7A:
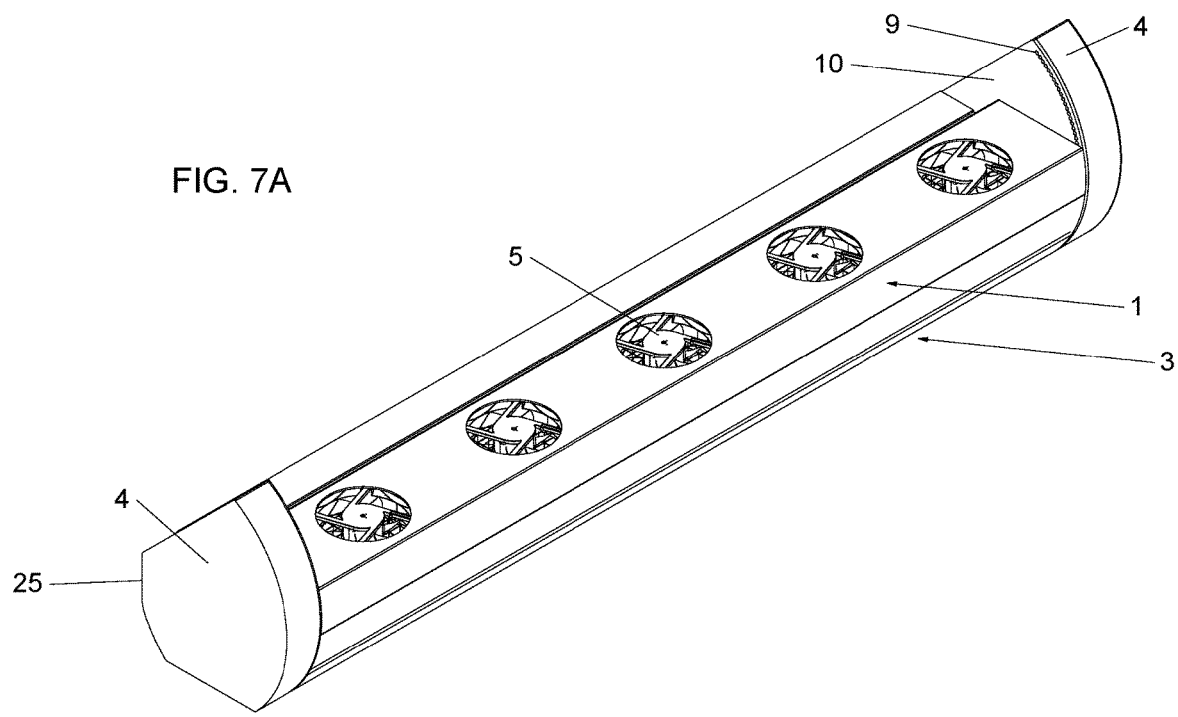
FIG. 7A shows a top perspective view of an example embodiment of germicidal light fixture configured for wall mounting and comprises one set of upper and lower baffle assemblies and one aperture.
Figure 7B:
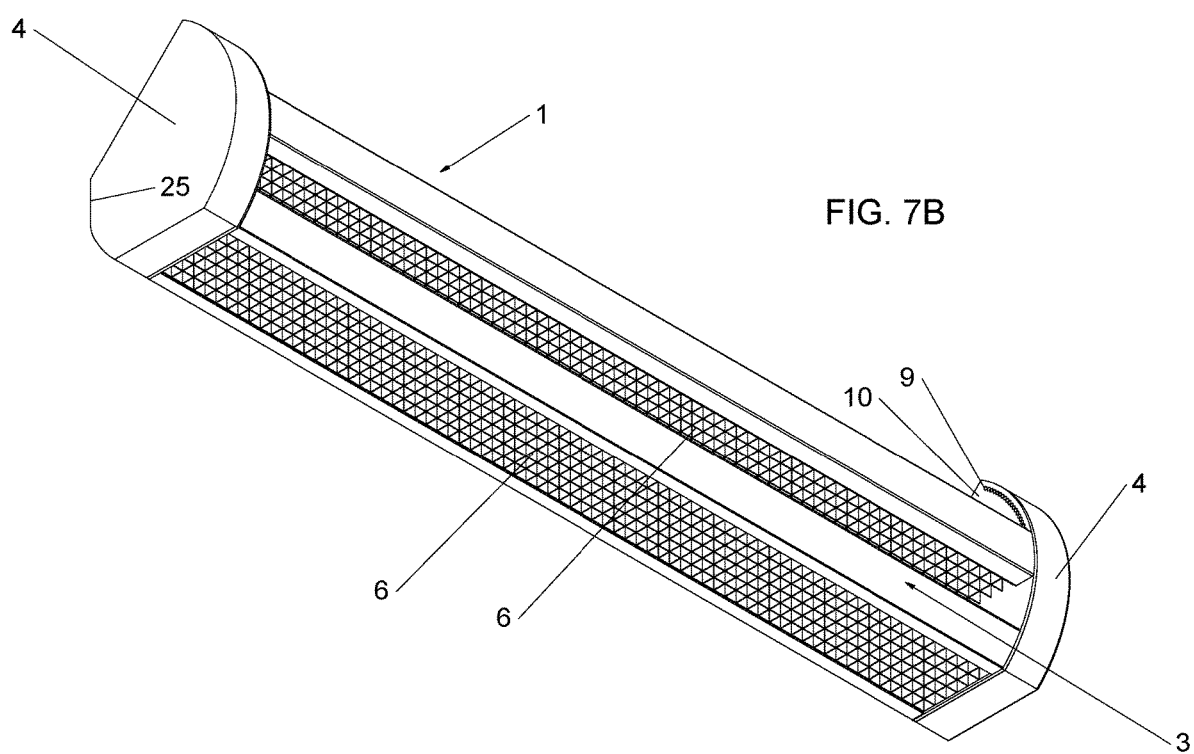
FIG. 7B shows a bottom perspective view of the example embodiment of germicidal light fixture configured for wall mounting as shown in FIG. 7A.
Figure 7C:
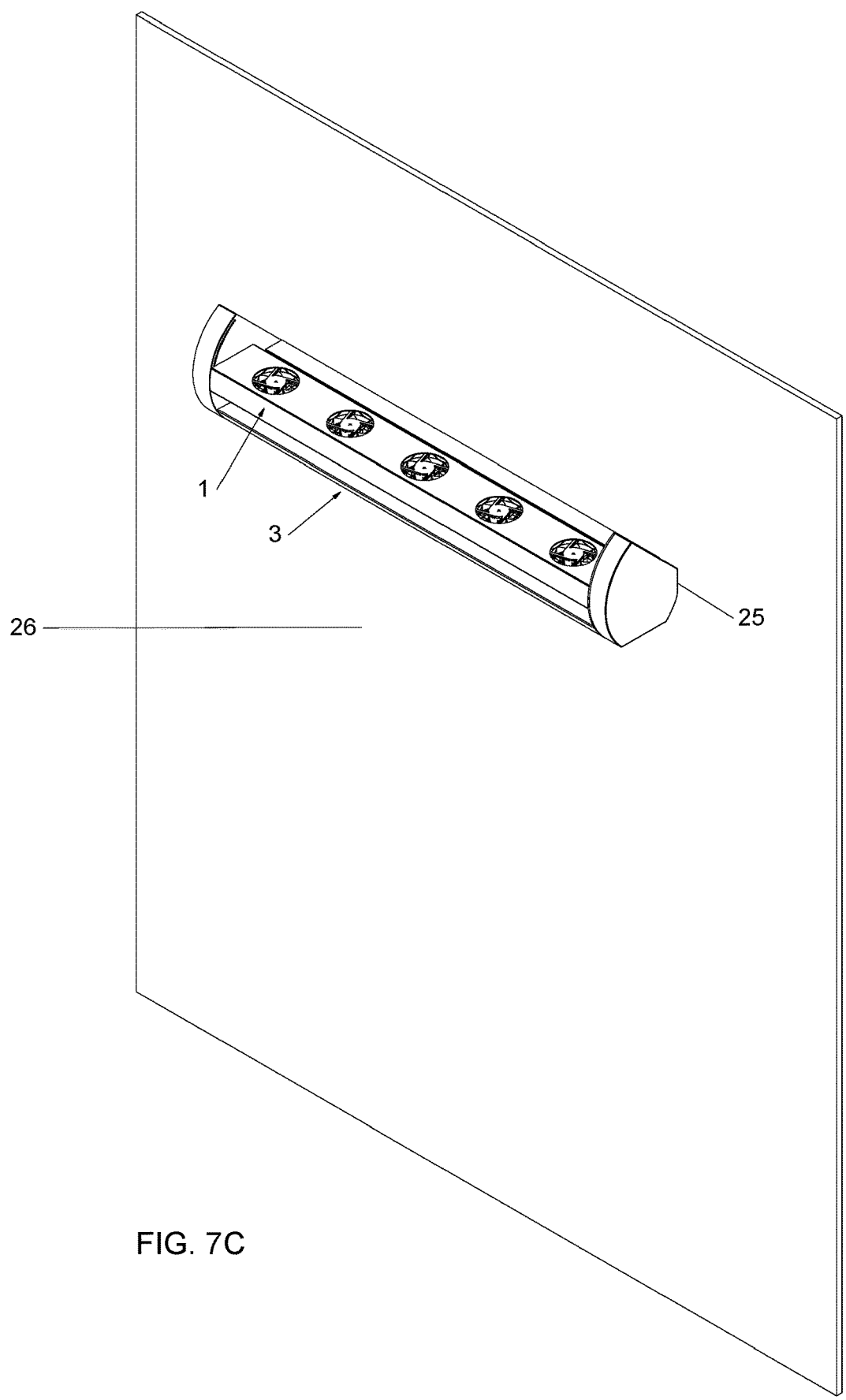
FIG. 7C shows a top perspective view of the example embodiment of the germicidal light fixture shown in FIG. 7A and is mounted on a wall.

FIG. 7A, FIG. 7B and 7C shows perspective views of an example embodiment of wall mounted GUV fixture. For brevity, features that are similar, or function in a similar manner to those already discussed may or may not be further discussed or referred to. Additionally, the operational principals and novel features of previously discussed example embodiments that are substantially similar may or may not be noted or discussed again for brevity. These example embodiments may comprise upper baffle assemblies 1, lower baffle assemblies 3, end caps 4, fans 5, egg crate louvers 6 upper baffle assembly positioning holes 9, end plates 10, and fixture mounting plate 25.

In an example embodiment, FIG. 7D shows a cross sectional profile view of a similar GUV fixture as shown in FIG. 7A, 7B and 7C, and may comprise upper baffle assemblies 1, lower baffle assemblies 3, end caps 4, fans 5, egg crate louvers 6, lower baffle assembly rails 7, upper baffle assembly rails 8, upper baffle assembly positioning holes 9, end plates 10, lamp 12, wall mounting plate 25 and reflector 13. Reflector 13 may comprise a parabolic or semi parabolic reflector or any other suitable reflector design that may function to direct as much UVC light out of the fixture aperture. It may be preferable to have the upper portion of the reflector 13 truncated to some degree at the top as shown, which may allow more UVC light to radiate upwards when the upper baffle assembly 1 is configured for high ceilings as previously discussed.

Figures 8A, 8B:
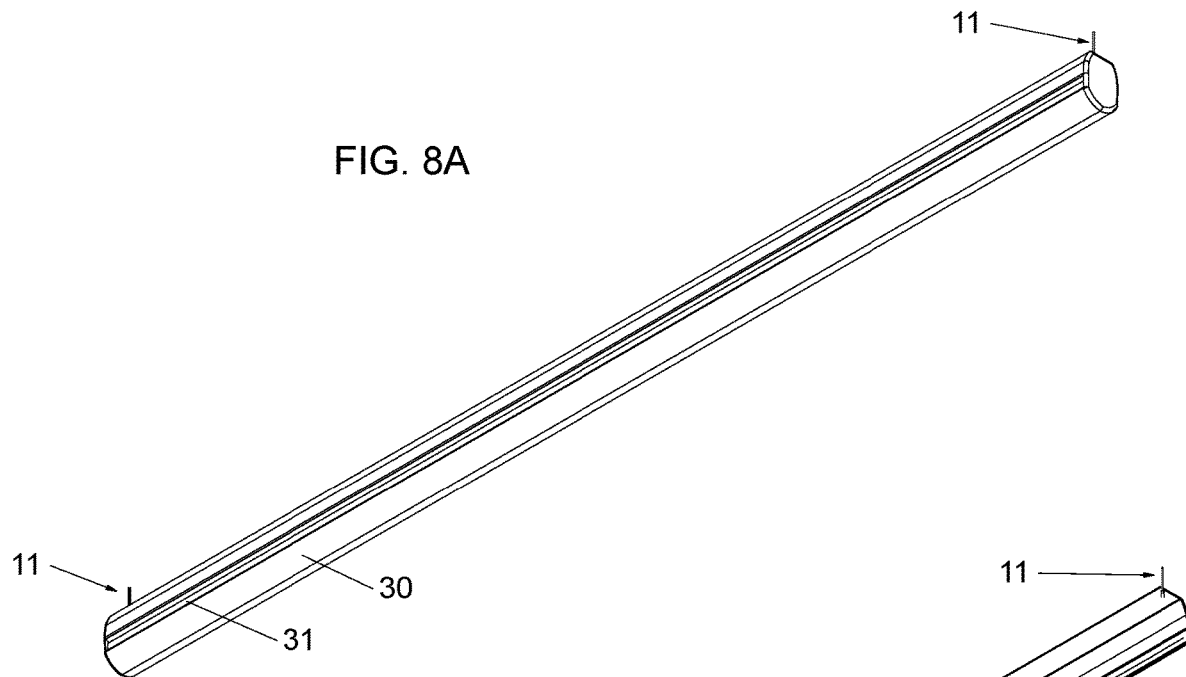
FIG. 8A shows a bottom perspective view of an example embodiment of germicidal light fixture comprising one or more TIR lenses.
FIG. 8B shows a top perspective view of the example embodiment of germicidal light fixture shown in FIG. 8A.
Figure 8C:
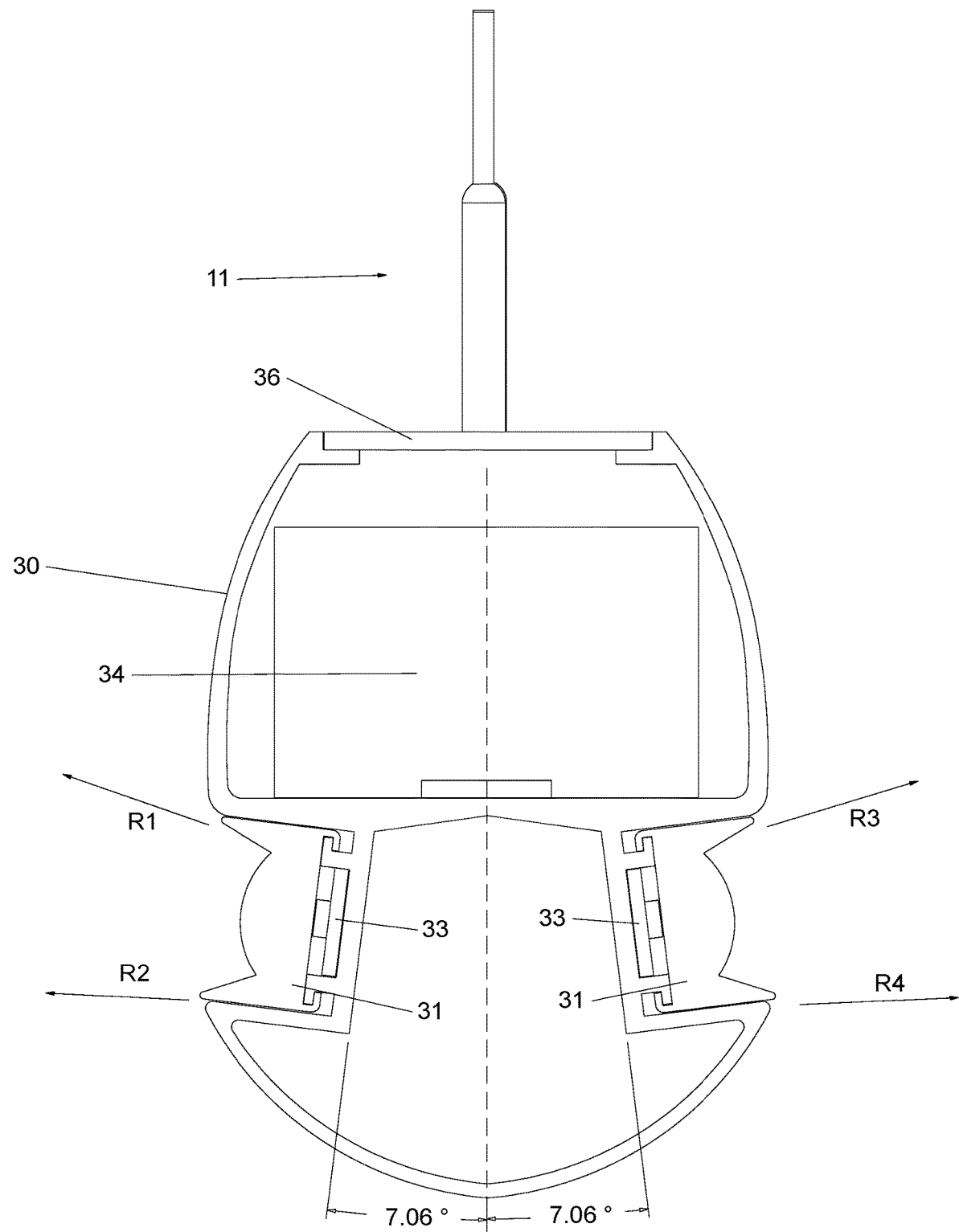
FIG. 8C shows an end view of the example embodiment of the germicidal light fixture shown in FIG. 8A with certain elements removed for illustrative purposes.

Example embodiments of novel GUV fixtures are shown in FIG. 8A, FIG. 8B and FIG. 8C that show a GUV light fixture configured with LED arrays with germicidal properties. FIG. 8A shows a bottom perspective view of an example embodiment that may comprise an aluminum extruded fixture body 30 that also functions as a heat sink for internally mounted LED arrays, a total internal reflection (TIR) lens 31 and hanger elements 11. FIG. 8B show a top perspective view of the same.

Referring to FIG. 8C in an example embodiment that is substantially similar to those shown in FIG. 8A and FIG. 8B, the fixture body 30 is shown. Extruded aluminum may be a cost effective and functionally superior fixture body because the entire body may function to dissipate heat generated by the LED arrays 33. Perhaps due to the generally low efficacy of germicidal LEDs at the time of this disclosure, said LED arrays may generate considerably more heat than LED arrays generating visible light. Adequate thermal management is therefore indicated. In example embodiments however, a fixture body may be fabricated utilizing any method or materials that may function adequately in a given application. For example, one or more parts of the fixture body 30 may comprise folded aluminum or steel sheet metal. One or more parts of the fixture body 30 may comprise thermally conductive polymers. One or more parts of the fixture body 30 may comprise a mixture of any of the above mentioned materials, methods or any other suitable materials or methods.

The LED arrays 33 may comprise any germicidal LED arrays that may be suitable for a given application. In an example embodiment, the LED arrays may be configured to emit UV as well as visible light and the fixture may be utilized as a traditional light fixture. Accordingly, although elements of the design and functionality may refer to example embodiments with reference to UVC or having germicidal properties, this should not be construed to limit the scope of example embodiments to only the field of germicidal applications.

TIR lenses 31 may be disposed directly in front of the LED arrays 33. TIR lens design and functionality are well known to those skilled in the art and will not be discussed in detail in this disclosure. The TIR lenses may be fabricated to collimate light from the LED arrays 33 to any beam angle that may be suitable to a given application. For example, in applications with a low ceiling height of 9 ft., it may be beneficial to have a beam angle of under 10 degrees.

Still referring to FIG. 8C, the dotted line may indicate the normal to the plane of a floor that may be disposed below an example embodiment of GUV fixture as shown. The LED arrays 33 and the TIR lenses 31 may be tilted upwards at an approximate 6-7-degree angle a notated. If the TIR lenses 31 comprise an approximate 10-degree beam angle (the angle between R1 and R2, and R3 and R4 respectively), the lower FWHM of the opposing beam angles may be slightly above parallel to the floor, wherein a majority of UVC emitted by the LED arrays may not be directed to occupants below the fixture. It should be noted however, that some light may still be directed downwards, and the radiant flux thereof may need to be verified as being below the prescribed safety limits for any occupants in the room. If exceeded, the TIR lenses 31 may be fabricated with a tighter beam angle, or each lens or TIR lens assembly may be designed to tilt upward at a greater angle. Mechanical shielding below and or above the TIR lenses 31 may also be utilized to create a hard cutoff such that no UVC may be directed below a chosen angle from the normal of the TIR lenses 31. Light source power supply 34, hanger assembly 11 and access plate are also shown.

Any TIR lenses discussed may be fabricated from linear style optics as shown, or individual optics that fit over one or more individual diodes.

Figure 10A:
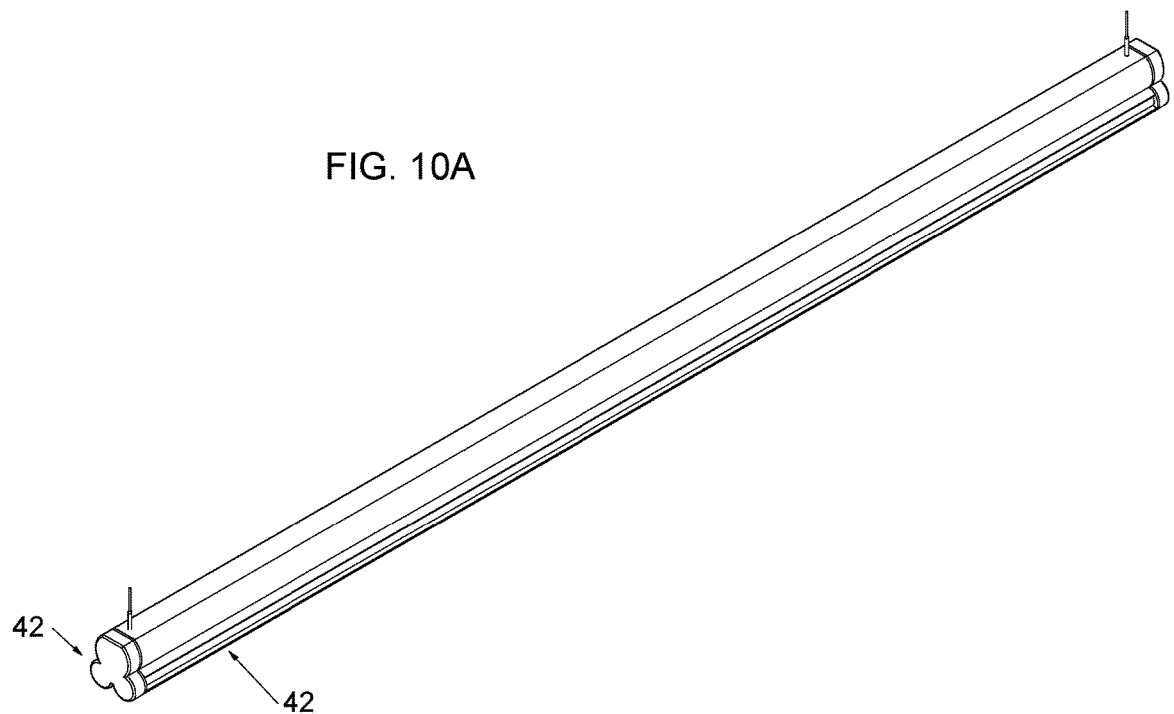
FIG. 10A shows a top perspective view of an example embodiment of germicidal light fixture comprising one or more rotating light engines.
Figure 10B:
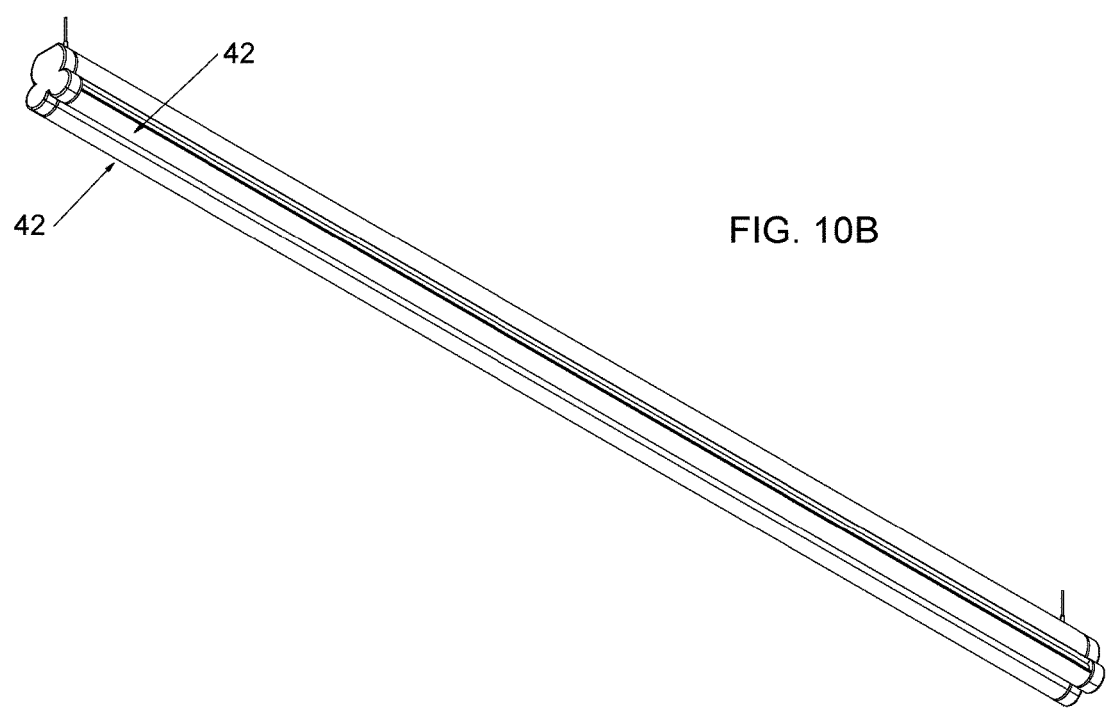
FIG. 10B shows a bottom perspective view of the example embodiment of the germicidal light fixture shown in FIG. 10A.

In an example embodiment, each TIR lens and LED array may be fabricated as an assembly configured with pivoting features incorporated on each end of the assembly wherein the angle of the assembly may be adjusted to different angles to accommodate rooms with different ceiling heights. FIG. 10A and FIG. 10B shows perspective views of an example embodiment. Pivoting UVC light engines 42 may be attached at each fixture end to end plates (FIG. 10D feature 46) that may enable the UVC light dispersion from the pivoting light engines 42 to be adjustably directed more towards the ceiling or floor for a given room application.

Figure 10D:
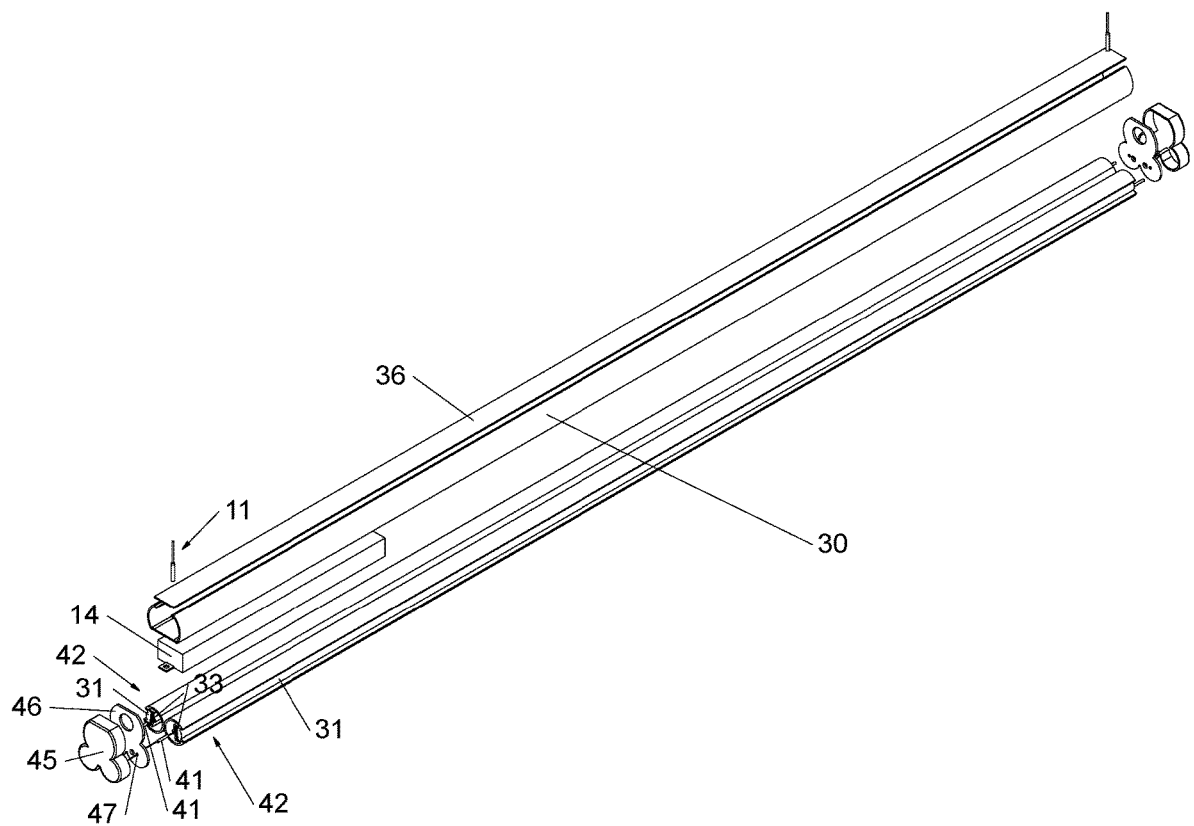
FIG. 10D shows an exploded view of the example embodiment of the germicidal light fixture shown in FIG. 10A.

FIG. 10C shows a profile view of the example embodiment shown in FIG. 10A and FIG. 10B with the end plates and end caps removed for illustrative purposes (FIG. 10D features 46 and 45). Pivoting light engines 42 may rotate in the direction of the arrows S and may comprise a body 49 that may also function as a heat sink for LED arrays 33. TIR lenses 31 may attach to the bodies 49. R1 through R4 may show a representative beam angle of the light refracted through the TIR lenses 31 in a similar manner as previously discussed. A main fixture body 30 may comprise access plate 36, hanger assemblies 11 and LED driver 14. The pivoting light engine bodies 49 may also comprise pivot pin holes to rotatingly engage pivot pins 41. Referring to FIG. 10D, pivot pins 41 may rotatingly engage to corresponding holes in the end plates 46 through pivot holes 47. Similar other features in FIG. 10D may be identified as are called out in FIG. 10A through FIG. 10C. Other suitable methods of enabling the light engines 42 to rotate may be utilized as would be obvious to those skilled in the art. Powe supply 14, access plate 36, hanger assemblies 11, lenses 31, ND LED arrays 33 are also shown.

Although example embodiments of GUV fixture such as those shown in FIG. 8A and FIG. 8B have been discussed using linear style TIR optics, this should not be construed to limit the range of possible optical designs for LEDs. For example, reflectors and lenses that collimate light into specific beam angles are available that fit over each individual diode. Generally, in such cases, each diode may be configured with higher light outputs in order to minimize the expense of multiple diode optics, as well as available space on a given pcb.

Although example embodiments in FIG. 10A through FIG. 10D are shown as pendant style hanging fixtures with UV light emitted from opposing sides of the fixtures, example embodiments of wall mounted versions may be configured in a similar manner as example embodiments shown in FIG. 1A and FIG. 1B that have been configured to a wall mounted version in FIG. 7A through FIG. 7C, wherein UV light may be only emitted on one side of the fixture.

Figure 9C:
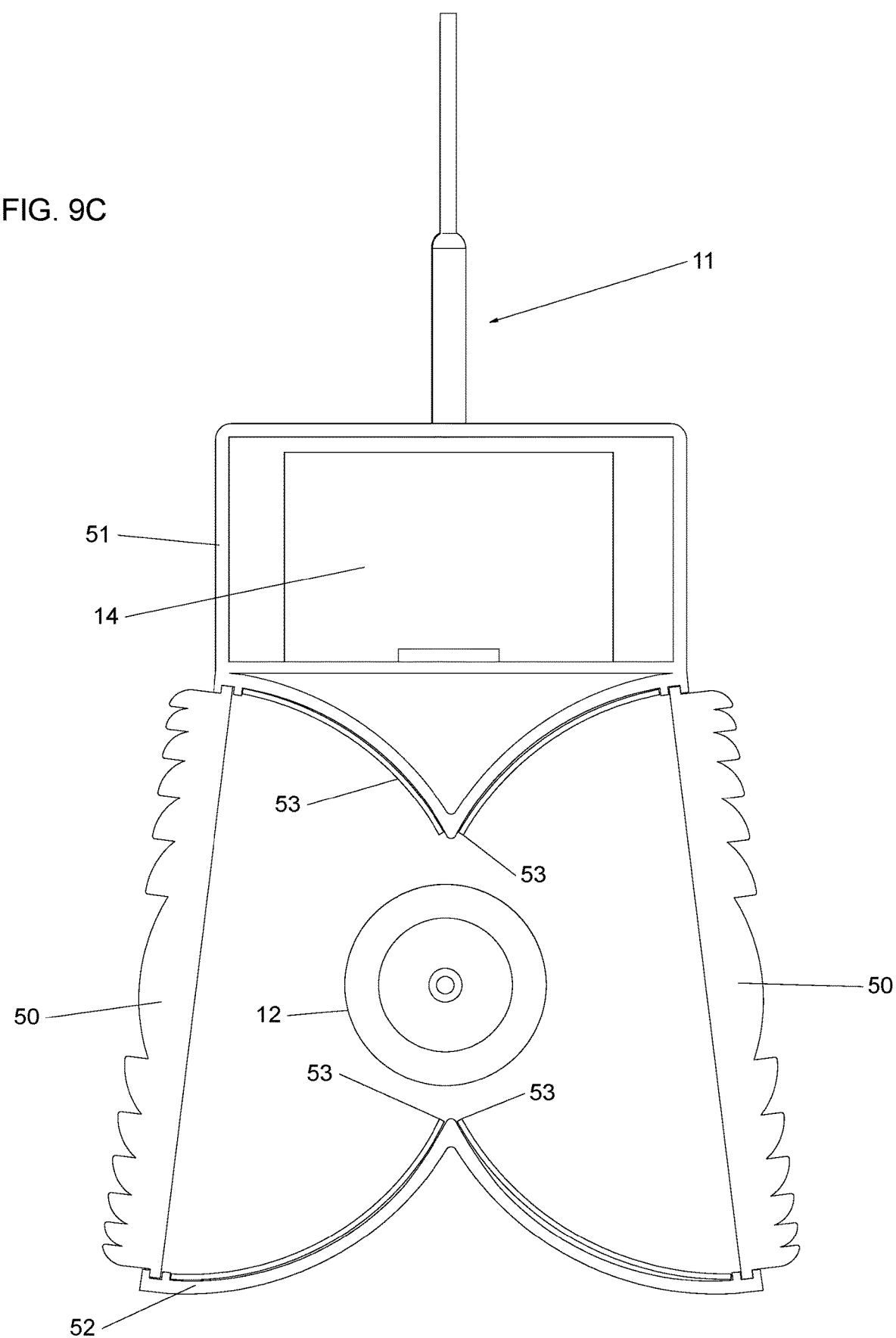
FIG. 9C shows an end view of the example embodiment of the germicidal light fixture shown in FIG. 9A with certain elements removed for illustrative purposes.

In example novel embodiments, a germicidal light source may be directed to semi-parabolic light collimating reflectors that may be directed to refract light through lenses such as Fresnel style lenses. FIG. 9A and FIG. 9B shows perspective views of an example embodiment comprising such features comprising lenses 50. Referring to FIG. 9C, a light source 12 may comprise a germicidal lamp such as a T5 or T8 style lamp for example, or any other light source discussed or otherwise suitable. Lower fixture body 52 and upper fixture body 51 may comprise light reflectors 53. Light reflectors 53 may be fabricated from any suitable material that may have high specular reflection efficiency and low absorption rates for the light frequency(s) emitted by the light source 12. The reflectors 53 shapes may be configured to best collimate the light from the light source 12 and direct the light towards the lenses 50. The fixture bodies 51 and 52 may also be configured to have shapes that may best optimize reflector efficiency as discussed. The functioning of parabolic and semi-parabolic reflectors as well as light collimating lenses are well known to those skilled in the art, and for brevity, will not be further discussed. In example embodiments as shown, and using high efficiency reflectors, the overall efficacy of the GUV fixture may be extremely high compared to fixtures currently on the market that utilize long slat type louvers as previously discussed. The lenses 50 may be configured from any suitable material such as quartz for example and may be configured with a refractive beam angle suitable to a given application. For example, a quartz or specially modified PMMA or silicon material may be utilized for a Fresnel type lens.

Although example embodiments in FIG. 9A through FIG. 9C are shown as pendant style hanging fixtures with UV light emitted from opposing sides of the fixtures, example embodiments of wall mounted versions may be configured in a similar manner as example embodiments shown in FIG. 1A and FIG. 1B that have been configured to a wall mounted version in FIG. 7A through FIG. 7C, wherein UV light may be only emitted on one side of the fixture.

In an example embodiment of the disclosed technology, a germicidal light fixture may comprise a light source configured to emit radiant flux, wherein the radiant flux may comprise properties capable inactivating one or more species of pathogen disposed in air. One or more lower baffle assemblies may be disposed substantially or partially adjacent and below the light source, and one or more upper baffle assemblies may be disposed substantially or partially adjacent and above the light source. One or more apertures may be defined by the openings between a corresponding set of upper and lower baffle assemblies, wherein radiant flux emitted by the light source can exit the fixture. The one or more lower and upper baffle assemblies may be configured to substantially block light rays emitted by the light source that are not on a trajectory to exit the one or more apertures.

In an example embodiment, the one or more upper and lower baffle assemblies may be configured to allow air to pass through them.

In an example embodiment, one or more of the one or more upper and lower baffle assemblies may comprise egg crate louvers.

In an example embodiment, one or more of the one or more upper and lower baffle assemblies may comprise air filter material.

In an example embodiment, one or more of the one or more upper and lower baffle assemblies may comprise a material that is configured to be air permeable, and also may have a high absorption rate with respect to the radiant flux emitted by the light source.

In an example embodiment, the germicidal light fixture may further comprise a bottom side configured to be oriented towards a floor in a room, and a top side configured to be oriented towards a ceiling in a room. The one or more upper baffle assemblies may comprise one or more fans, wherein the one or more fans may be configured to pull room air through the one or more lower baffle assemblies and the one or more apertures, and may disperse the air out the top side of the fixture.

In an example embodiment, the germicidal light fixture may comprise two upper baffle assemblies wherein each upper baffle assembly may substantially oppose each other, and may further comprise two lower baffle assemblies substantially opposed to each other, and wherein the space between each opposing set of upper and lower baffle assemblies may define two opposing apertures, and wherein the fixture may be configured to be hung from a ceiling.

In an example embodiment, the germicidal light fixture may comprise one upper baffle assembly and one lower baffle assembly which may define a single aperture, and wherein the fixture may be configured to mount on a wall.

In an example embodiment, the one or more upper baffle assemblies may be configured to be adjustable, wherein the one or more apertures may be increased or decreased in size through the angular orientation of the one or more upper baffle assemblies.

In an example embodiment, the light source may be one or more UVC lamps.

In an example embodiment, the light source may be one or more UVC LED arrays.

In an example embodiment, the light source may be one or more krypton chlorine excimer lamps.

In an example embodiment, the germicidal light fixture may further comprise a reflector partially disposed around the light source, wherein the reflector may be configured to direct a portion of the radiant flux emitted by the light source towards the one or more apertures.

In an example embodiment of the disclosed technology, a germicidal light fixture may comprise a fixture body configured to engage one or more light engines, and may further comprise one or more light engines. Each light engine may comprise one or more LED arrays configured to emit radiant flux, wherein the radiant flux may comprise properties capable inactivating one or more species of pathogen disposed in air. One or more lenses may be disposed in front of the one more LED arrays, or in front of one or more individual diodes in the one or more LED arrays, wherein the one or more lenses may be configured with total internal reflection properties configured to collimate the radiant flux emitted by the one or more LED arrays. The one or more light engines may further comprise one or more light engine bodies configured to engage a corresponding one or more LED array and a one or more lens, wherein the radiant flux refracted through the one or more lenses may be configured to contact air surrounding the germicidal light fixture.

In an example embodiment, the germicidal light fixture may have two light engines that are substantially opposed to each other, and the germicidal light fixture may be configured to hang from a ceiling.

In an example embodiment, the germicidal light fixture may have one light engine and the germicidal light fixture may be configured to mount on a wall.

In an example embodiment, the one or more light engine bodies may further comprise a pivot feature on two opposing ends which may allow the one or more light engines to rotate in at least one plane.

In an example embodiment of the disclosed technology, a germicidal light fixture may comprise a light source configured to emit radiant flux, wherein the radiant flux may comprise properties capable inactivating one or more species of pathogen disposed in air. The fixture may further comprise at least one light collimating lens disposed adjacent to the light source and a fixture body configured to engage the at least one light collimating lens and the light source. The radiant flux refracted through the one or more lenses may be configured to contact air surrounding the germicidal light fixture.

In an example embodiment, the germicidal light fixture may further comprise two opposing light collimating lenses and an upper and lower reflector disposed above and below the light source. The two reflectors together may form two semi-parabolic reflectors configured to collimate light from the light source and direct it to each opposing light collimating lens.

In an example embodiment, the germicidal light fixture may have two light collimating lenses that are substantially opposed to each other, and the germicidal light fixture may be configured to hang from a ceiling.

In an example embodiment, the germicidal light fixture may have one light collimating lens and the germicidal light fixture may be configured to mount on a wall.

In an example embodiment of the disclosed technology, a germicidal light fixture may comprise an upper room air germicidal UV light fixture configured to irradiate air with UVC light in an upper portion of a room, wherein the radiant flux from the fixture may be substantially directed to the portion of the room air that is defined by the boundaries of approximately seven feet above the floor and the ceiling of the room. The upper room air germicidal UV light fixture may further comprise one or more fans attached to the upper room air germicidal UV light fixture, wherein the fans may be configured to increase the volume of room air that contacts radiant UVC flux emitted by the upper room air germicidal UV light fixture.

I claim:

1. An upper room air germicidal light fixture comprising:
a light source configured to emit light, wherein the light is emitted at wavelengths capable of inactivating at least one species of pathogen disposed in air;
at least one lower baffle assembly disposed adjacent to the light source wherein said at least one lower baffle assembly enables air to flow through said at least one lower baffle assembly, wherein said at least one lower baffle is also configured to direct the light and to block or substantially dissipate incident light rays from the light source;
at least one upper baffle assembly disposed adjacent to the light source wherein said at least one upper baffle assembly enables air to flow through said at least one upper baffle assembly, wherein said at least one upper baffle is also configured to direct the light and to block or substantially dissipate incident light rays from the light source; and at least one aperture defined by an opening between a corresponding set of upper and lower baffle assemblies, wherein the light emitted by the light source exits the fixture through said at least one aperture simultaneously in multiple directions, wherein, when the germicidal light fixture is disposed in a room, surrounding room air will contact light exiting the apertures of said fixture, and room air traveling through said fixture will contact light inside and between the corresponding set of upper and lower baffle assemblies, and wherein the at least one upper baffle assembly is adjustable, such that a size of the at least one aperture is adjustable based on an angular orientation of the at least one upper baffle assembly relative to the lower baffle assembly.

2. The germicidal light fixture of claim 1, wherein at least one of the at least one upper baffle assembly and the at least one lower baffle assembly comprises egg crate louvers.

3. The germicidal light fixture of claim 1, wherein at least one of the at least one upper baffle assembly and the at least one lower baffle assembly comprises a material configured to be air permeable and has an absorption rate above a predetermined threshold for the wavelengths of the light emitted by the light source.

4. The germicidal light fixture of claim 1, wherein the at least one upper baffle assembly comprises at least one fan, wherein the at least one fan is configured to pull room air through the at least one lower baffle assembly and through the at least one aperture, and wherein the at least one fan is configured to disperse the air towards a ceiling in a room.

5. The germicidal light fixture of claim 1, further comprising a second corresponding set of upper and lower baffle assemblies adjacent to the corresponding set of upper and lower baffle assemblies, and wherein a second aperture is defined by the second corresponding set of upper and lower baffle assemblies the space between each opposing set of upper and lower baffle assemblies defines two opposing apertures, wherein the fixture is configured to be hung from a ceiling.

6. The germicidal light fixture of claim 1, wherein the at least one upper baffle assembly comprises one upper baffle assembly, wherein the at least one lower baffle assembly comprises one lower baffle assembly, wherein a single aperture is defined by a space between the one upper baffle assembly and the one lower baffle assembly, and wherein the fixture is configured to mount on a wall.

7. The germicidal light fixture of claim 1, wherein the light source is at least one of UV lamps, UV LED arrays, and krypton chlorine excimer lamps.

8. The germicidal light fixture of claim 1, further comprising a reflector partially disposed around the light source, wherein the reflector is configured to direct a portion of the light emitted by the light source towards the at least one aperture.

9. A germicidal light fixture comprising:

an upper room air germicidal light fixture configured to irradiate air with light in an upper portion of a room wherein:

the light is emitted at wavelengths capable of inactivating at least one species of pathogen disposed in air;

the upper room air germicidal UV light fixture comprises at least one baffle assembly configured to direct the light out of the fixture simultaneously in multiple directions;

the light from the fixture is substantially directed to portions of the room air that is are substantially adjacent to or above said fixture; and the upper room air germicidal UV light fixture comprises at least one fan, wherein the at least one fan is configured to increase the volume of room air that contacts the light emitted by the upper room air germicidal UV light fixture, wherein the at least one baffle assembly is adjustable such that a size of at least one aperture defined by the at least one baffle assembly is adjustable based on an angular orientation of the at least one baffle assembly; and wherein the at least one baffle assembly comprises at least one upper baffle assembly and at least one lower baffle assembly, wherein a single aperture is defined by a space between one upper baffle assembly and one lower baffle assembly.

10. The germicidal light fixture of claim 9, wherein the at least one baffle assembly comprises egg crate louvers.

11. The germicidal light fixture of claim 9, wherein the at least one baffle assembly comprises a material that is configured to be air permeable and that has an absorption rate above a predetermined threshold for the wavelengths of light emitted by the light source.

12. The germicidal light fixture of claim 9, wherein the at least one baffle assembly comprises two corresponding sets of upper and lower baffle assemblies adjacent to and substantially opposed to each other wherein spaces between each set of upper and lower baffle assemblies define two apertures therebetween, and wherein the fixture is configured to be hung from a ceiling.

13. The germicidal light fixture of claim 9, wherein the fixture is configured to mount on a wall.

14. The germicidal light fixture of claim 9, wherein the light source is at least one of UV lamps, UV LED arrays, and krypton chlorine excimer lamps.

* * * * *